US006103893A

United States Patent [19]
Cooke et al.

[11] Patent Number: 6,103,893
[45] Date of Patent: Aug. 15, 2000

[54] HIGH AMYLOSE STARCH FROM TRANSGENIC POTATO PLANTS

[75] Inventors: David Cooke, Oakley; Michael John Gidley, Raunds; Stephen Alan Jobling, Huntingdon; Richard Safford; Christopher Michael Sidebottom, both of Bedford; Roger J. Westcott, Wellingborough, all of United Kingdom

[73] Assignee: National Starch and Chemical Investment Holding Corporation, Wilmington, Del.

[21] Appl. No.: 08/716,449

[22] PCT Filed: Mar. 22, 1995

[86] PCT No.: PCT/GB95/00634

§ 371 Date: Sep. 24, 1996

§ 102(e) Date: Sep. 24, 1996

[87] PCT Pub. No.: WO95/26407

PCT Pub. Date: Oct. 5, 1995

[30] Foreign Application Priority Data

Mar. 25, 1994 [GB] United Kingdom .................. 9406022
Aug. 4, 1994 [EP] European Pat. Off. .............. 94305806
Jan. 13, 1995 [EP] European Pat. Off. .............. 95300210

[51] Int. Cl.$^7$ ............................ C08B 30/00; C08B 30/04; C08B 30/20
[52] U.S. Cl. .............................................. 536/102; 536/128
[58] Field of Search ................................ 435/91.1, 91.3, 435/93, 193, 101, 172.1, 172.3, 410, 417, 429, 320.1, 98, 210, 468, 469, 470; 514/44; 436/20; 536/23.2, 24.5, 102, 128; 800/205, 284, 286; 935/35

[56] References Cited

U.S. PATENT DOCUMENTS 4,971,723 11/1990 Chiu ....................................... 252/315.3
5,585,479 12/1996 Hoke et al. .............................. 536/24.5
5,856,467 1/1999 Hofvander et al. ........................ 536/45

FOREIGN PATENT DOCUMENTS

WO 92/11375 7/1992 WIPO.
WO 92/14827 9/1992 WIPO.

OTHER PUBLICATIONS

Abel et al. Manipulation of Starch Biosynthesis and the Structure of Starch in Transgenic Potato Plants. Royal Society of Chemistry Publication No. 205, Fraizier et al, eds. 1997.
Zobel, H. F. Gelatinization of starch and mechanical properties of starch pastes, in "Starch: Chemistry and Technology", Whistler et al., eds. New York, Academic Press, Inc, pp. 285–309, 1984.
Gewirtz et al. Facilitating oligonucleotide delivery: helping antisense deliver on its promise. Proc. Natl. Acad. Sci. USA 93: 3161–3163, Apr. 1996.
Abstracts VIIth International Congress on Plant Tissue and Cell Culture, Amsterdam, Jun. 24–29, 1990, Abstrract No. AS–28, F.R. van der Leij et al. "Expression of the Gene Encoding Granule–Bound Starch Synthase after Introduction inan Amylose–Free and a Wildtype Potato (Solanum Tuberosum)".
Proc. Internat. Symp. Plant Polymeric Carbohydrates, 1992, pp. 33–39, L. Willmitzer et al., "Starch Synthesis in Transgenic Plants".
Plant Physiol., vol. 102, 1993, pp. 1053–1054, P. Poulsen and J.D. Kreiberg; "Starch Branching Enzyme cDNA from Solanum Tuberosum".
Febs Letters, vol. 332, 1992, pp. 132–138, J. Khoshnoodi, et al., "Characterization of the 97 and 103 kDa Forms of Starch Branching Enzyme from Potato Tubers".
Molec. Gen. Genet, vol. 225, 1991, pp. 289–296, R.G.F. Visser, et al., "Inhibition of the Expression of the Gene for Granule–Bound Starch Synthase in Potato Antisense Constructs".

*Primary Examiner*—David Guzo
*Assistant Examiner*—Thomas G. Larson
*Attorney, Agent, or Firm*—Karen G. Kaiser

[57] ABSTRACT

Disclosed is a method of producing altered starch from transformed potato plants or their progeny, comprising extracting starch from a potato plant, at least the tubers of which comprise at least an effective portion of a starch branching enzyme (SBE) cDNA sequence operably linked in the antisense orientation to a suitable promoter, such that the level of SBE activity is limited to less than 0.8 units per gram tuber. Also disclosed are potato plants comprising altered starch in accordance with the invention.

19 Claims, 7 Drawing Sheets

HIGH AMYLOSE STARCH FROM TRANSGENIC POTATO PLANTS

FIELD OF THE INVENTION

This invention relates to a method of obtaining novel types of starch from potato plants, to novel potato plants from which the starch may be obtained, and to vectors for obtaining said plants.

BACKGROUND OF THE INVENTION

Starch is the major form of carbon reserve in plants. constituting 50% or more of the dry weight of many storage organs—e.g. tubers. seeds of cereals. Starch is used in numerous food and industrial applications. In many cases, however. it is necessary to modify the native starches, via chemical or physical means. in order to produce distinct properties to suit particular applications. It would be highly desirable to be able to produce starches with the required properties directly in the plant, thereby removing the need for additional modification. To achieve this via genetic engineering requires knowledge of the metabolic pathway of starch biosynthesis. This includes characterisation of genes and encoded gene products which catalvse the synthesis of starch. Knowledge about the regulation of starch biosynthesis raises the possibility of re-programming biosynthetic pathways to create starches with novel properties that could have new commercial applications.

The commercially useful properties of starch derive from the ability of the native granular form to swell and absorb water upon suitable treatment. Usually heat is required to cause granules to swell in a process known as gelatinisation, which has been defined (W. A. Atwell et al., Cereal Foods World 33, 306–311. 1988) as " . . . the collapse (disruption) of molecular orders within the starch granule manifested in irreversible changes in properties such as granular swelling, native crvstallite melting, loss of birefringence. and starch solubilisation. The point of initial gelatinisation and the range over which it occurs is governed by starch concentration, method of observation, granule type, and heterogeneities within the granule population under observation". A number of techniques are available for the determination of gelatinisation as induced by heating, a convenient and accurate method being differential scanning calorimetry, which detects the temperature range and enthalpy associated with the collapse of molecular orders within the granule. To obtain accurate and meaningful results, the peak temperature of the endotherm observed by differential scanning calorimetry is usually determined.

The consequence of the collapse of molecular orders within starch granules is that the granules are capable of taking up water in a process known as pasting, which has been defined (W. A. Atwell et al., Cereal Foods World 33, 306–311, 1988) as ". . . the phenomenon following gelatinisation in the dissolution of starch. It involves granular swelling, exudation of molecular components from the granule. and eventually. total disruption of the granules". The best method of evaluating pasting properties is considered to be the viscoamylograph (Atwell et al., 1988) in which the viscosity of a stirred starch suspension is monitored under a defined time/temperature regime. A typical viscoamylograph profile for potato starch is shown in FIG. 5, in which the initial rise in viscosity is considered to be due to granule swelling. At a certain point, defined by the viscosity peak, granule swelling is so extensive that the resulting highly expanded structures are susceptible to mechanically-induced fragmentation under the stirring conditions used. With increased heating and holding at 95° C. further reduction in viscosity is observed due to increased fragmentation of swollen granules. This general profile (FIG. 5) has previously always been found for native potato starch. In addition to the overall shape of the viscosity response in a viscoamylograph, a convenient quantitative measure is the temperature of initial viscosity development (onset). FIG. 2 shows a typical viscosity profile for starch (Kennedy & Cabalda, Chem. in Britain. November 1991, 1017–1019), during and after cooking, with a representation of the physical state of the starch granules at various points. The letters A, B, C and D correspond to the stages of viscosity onset (A), maximum viscosity (B), complete dispersion (C) and re-association of molecules (or retrogradation, D).

The properties of potato starch are useful in a variety of both food and non-food (paper, textiles, adhesives etc.) applications. However, for many applications, properties are not optimum and various chemical and physical modifications well known in the art are undertaken in order to improve useful properties. Two types of property manipulation which would be of use are firstly the controlled alteration of gelatinisation and pasting temperatures and, secondly, starches which do not suffer as much granular fragmentation during pasting as illustrated in FIG. 1. Currently the only ways of manipulating the gelatinisation and pasting temperatures of potato starch are by the inclusion of additives such as sugars, polyhydroxy compounds of salts (Evans and Haisman, Starke 34, 224–231, 1982) or by extensive physical or chemical pre-treatments (e.g. Stute, Starke 44, 205–214, 1992). The reduction of granule fragmentation during pasting can be achieved either by extensive physical pre-treatments (Stute, Starke 44, 205–214, 1992) or by chemical cross-linking. Such processes are inconvenient and inefficient. It is therefore desirable to obtain plants which produce starch which intrinsically possesses such advantageous properties.

Starch Biosynthesis

Starch consists of 2 major components: amylose, a linear polymer of alpha, 1–4 linked glucose units; and amylopectin, a branched polvmer consisting of an alpha, 1–4 linked glucan backbone with alpha, 1–6 linked branches. The key enzymes in starch biosynthesis are the starch synthases and starch branching enzyme [alpha-1,4-glucan: alpha-1,4-glucan 6-glucosyltransferase. EC 2.4.1.18]. Amylose is synthesized from adenosine 5'-(alpha-D-glucopyranosyl pyrophosphate), or "ADP-glucose", by a starch synthase which is associated with the starch granule: the so-called "granule bound starch synthase" (GBSS). Amylopectin is synthesized from ADP-glucose by the concerted action of a soluble starch synthase (SSS) and starch branching enzyme (SBE). SBE hydrolyses the linear alpha-1–4 glucan chain and rejoins the cleaved portion via an alpha-1–6 linkage to produce a branched structure. The activity of SBE is thus of crucial importance in determining the type, and hence properties, of starch synthesized within plant systems.

Starch Branching Enzyme

In most plant species, SBE occurs in multiple forms (e.g. maize kernels. Boyer & Preiss, Biochem. Biophys. Res. Commun. 80, 169–175 (1978); sorghum seed, Boyer, Phytochem. 24, 15–18 (1985); rice endosperm, Smyth. Plant Sci. 57, 1–8 (1988); pea embryo, Smith, Planta 175, 270–279 (1988)). However, in potato tuber, only a single form of SBE has so far been identified (Blennow & Johansson, Phytochem. 30, 437–444 (1991)).

Endosperm of maize contains three forms of SBE, namely SBE I, SBE IIa and SBE IIb. The "amylose extender" (ae)

mutation causes a large reduction of SBE activity and in particular loss of SBE IIb. This reduction in SBE activity results in a higher ratio of amylose to amylopectin in endosperm starch compared to normal maize (Boyer & Preiss, Biochem. Biophys. Res. Commun. 80, 169–175 (1978)).

In pea embryos, 2 forms of SBE exist. The r (wrinkled) mutant of pea lacks SBE I activity and starch from this source has a higher ratio of amylose to amylopectin than normal peas [Smith, Planta 175, 270–279 (1988)].

In potato, amylose-free mutants have been obtained by X-ray irradiation (Hoverkamp-Hermelink et al., Theor. Appl. Genet. 75, 217–221, 1987) and by transformation with antisense-GBSS constructs (Visser et al., Mol. Gen. Genet. 225, 289–296, 1991). However, no high amylose mutants of potato exist and efforts to produce such via transformation with antisense SBE constructs have, hitherto, been unsuccessful (e.g. DE 41 04782A1). In respect of the latter, Wilmitzer et al., [Proceedings International Symposium on Plant Polymeric Carbohydrates, ed. Meuser. Manners & Siebel (1992) pp 33–39] have, using antisense SBE technology, produced tubers containing only 10–20% SBE activity of control tubers, but: "neither the amylose content of the starch in the tubers of these plants, nor the total starch content of the tubers, was altered" (p.39). Similarly, WO 92/11375 suggests the use of an anti-sense approach to alter the starch content of tubers, but there was no reduction to practice and no data showing success of the approach, which disclosure cannot therefore be considered as enabling.

The present inventors have been able to employ similar techniques to obtain plants with even lower levels of SBE activity than those described by Wilmitzer. Surprisingly, especially in view of Wilmitzer's results, the starch obtained from such plants has unexpected novel, commercially useful properties.

SUMMARY OF THE INVENTION

In a first aspect the invention provides a method of producing altered starch from transformed potato plants or their progeny, the method comprising extracting starch from a potato plant, at least the tubers of which comprise at least an effective portion of a starch branching enzyme (SBE) cDNA sequence operably linked in the antisense orientation to a suitable promoter, such that the level of SBE activity is limited to less than 0.8 units per gram tuber.

A unit of SBE activity is defined below.

It is believed that "antisense" methods are mainly operable by the production of antisense mRNA which hybridises to the sense mRNA, preventing its translation into functional SBE polypeptide (eg. Sheehy et al; 1988 PNAS 85, 8805–8809, Van der Rrol et al; Mol. Gen. Genet. 220, 204–212). Thus, it will be apparent to those skilled in the art that neither a full length SBE cDNA sequence nor a "native" SBE cDNA sequence is essential. Preferably the effective portion of an SBE cDNA sequence comprises at least ⅔ of a full length cDNA sequence, but by simple trial and error, other fragments (smaller or larger) may be found which are functional in limiting the SBE activity to less than 0.8 units per gram tuber. Similarly, the SBE cDNA sequence could be a variant comprising several base mismatches (scattered throughout the sequence or concentrated in a few regions) compared to a native SBE cDNA sequence, yet still give rise to an mRNA molecule capable of inhibiting the translation of mRNA derived from the sense strand of an SBE coding sequence. Such fragments and variants are within the scope of the invention.

It will also be apparent to those skilled in the art that the sequence need not be a cDNA sequence according to the strict sense of the term, in that the sequence used could be an equivalent derived from a genomic SBE encoding sequence, although such genomic sequences will preferably be adapted (e.g. by the removal of intron sequences).

Altered starch produced according to the method of the invention is found to have the following physical properties:
 a) elevated peak temperature of gelatinisation as determined by differential scanning calorimetry (DSC) relative to unaltered starch produced from equivalent non-transformed plants; and
 b) elevated viscosity onset temperature, relative to unaltered starch produced from equivalent non-transformed plants.

The altered starch possesses these qualities ab initio as first extracted from the potato plant: the properties are not, for example, acquired by heating in the extraction process.

In a further aspect, the invention thus provides altered starch extracted from transformed potato plants or their progeny having less than 0.8 units SBE activity per gram tuber, the altered starch as extracted preferably having ab initio the properties defined above.

The parameters given above are frequently used by those skilled in the art to determine the properties of starch. The Examples below describe particular assay methods by which these parameters may be determined.

The peak temperature of gelatinisation is the temperature at which there is a maximum in the loss of order in granules within a sample of starch in the presence of excess water, as judged by the heat flow required to maintain a constant rate of temperature increase, compared with a sample of water. Preferably the peak temperature of gelatinisation is elevated by at least 2° C. more preferably by at least 5° C., compared to unaltered starch.

For the purposes of the present specification, the viscosity onset temperature is defined as the temperature at which the viscosity of a 10% w/w aqueous starch solution becomes at least 50% greater than the maximum viscosity of the solution at lower temperatures (above 50° C.). Viscosity may be measured in arbitrary units (e.g. instrument stirring number units or "SNU"). Preferably the viscosity onset temperature is elevated by at least 3° C., and more preferably by at least 5° C. compared to unaltered starch.

Preferably the altered starch produced from the transformed plants (or the progeny thereof) has a peak temperature of gelatinisation (as determined by differential scanning caloriometry) of at least 71° C. and/or a viscosity onset temperature of at least 71° C.

Preferably the plants used in the method comprise a full length SBE cDNA sequence operably linked in the antisense orientation to a suitable promoter.

The altered starch is extracted from potato plants in which the starch branching enzyme (SBE) activity is less than 0.8 units per gram tuber. (A unit of activity is defined for present purposes as the amount of enzyme activity which incorporates into starch 1 micromole of glucose per minute at a temperature of 30° C.)

Preferably the altered starch is extracted from the plant by wet milling of potato tubers.

Preferably the altered starch is obtained from transformed potato plants or their progeny, the tubers of which exhibit less than 10%, and preferably less than 5%, of SBE activity compared to equivalent non-transformed control plants.

In a further aspect, the invention provides a vector for modifying a potato plant so as to cause the plant to be capable of giving rise to tubers having less than 0.8 units SBE activity per gram tuber, the vector comprising at least an effective portion of an SBE cDNA sequence operably linked in the antisense orientation to a suitable promoter.

Preferably the vector comprises a full length SBE CDNA sequence, preferably that of potato SBE, operably linked in the antisense orientation to a suitable promoter. Suitable promoters include the CaMV 35S and the GBSS promoters. In a preferred embodiment the vector comprises a plurality of copies of the CaMV 35S promoter, preferably operably linked in a tandem arrangement.

In another aspect the invention provides a potato plant capable of giving rise to tubers having less than 0.8 units SBE activity per gram tuber and comprising at least an effective portion of an SBE cDNA sequence operably linked in the antisense orientation to a suitable promoter. Typically, such a plant will have been transformed with an antisense SBE construct, or will be the progeny of such a plant.

Preferably the plant tubers exhibit less than 10%. more preferably less than 5%, of the SBE activity of equivalent non-transformed control plants.

BRIEF DESCRIPTION OF THE DRAWINGS

The various aspects of the invention will now be further illustrated by way of example and with reference to the drawings, of which:

FIG. 8 shows the sequence, SEQ ID NO. 1, of a full length potato SBE cDNA clone.

EXAMPLES

Example 1

Figure 1:
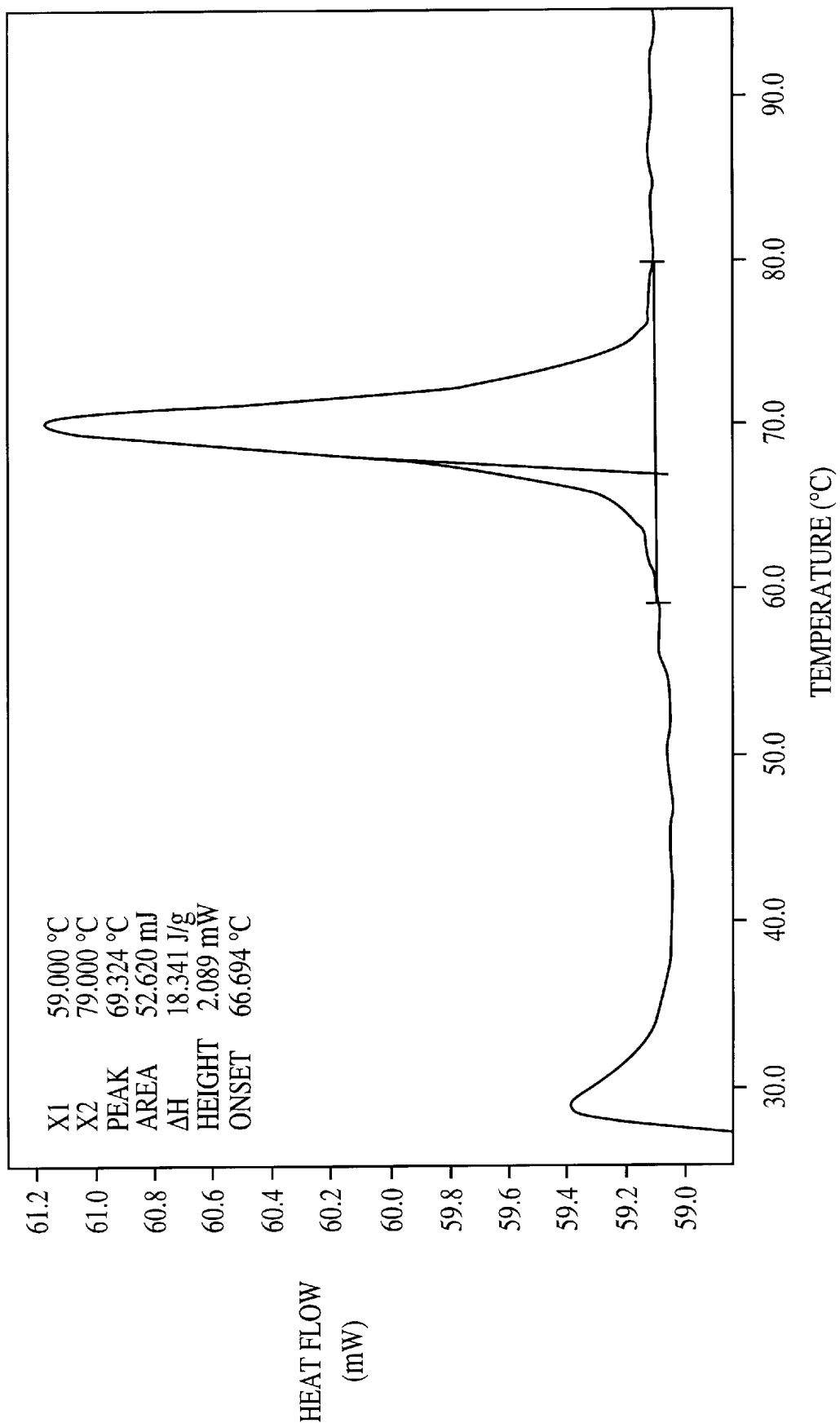
FIG. 1 shows how the degree of gelatinisation of an unaltered starch sample varies with temperature, as measured by differential scanning calorimetry.
Figure 2:
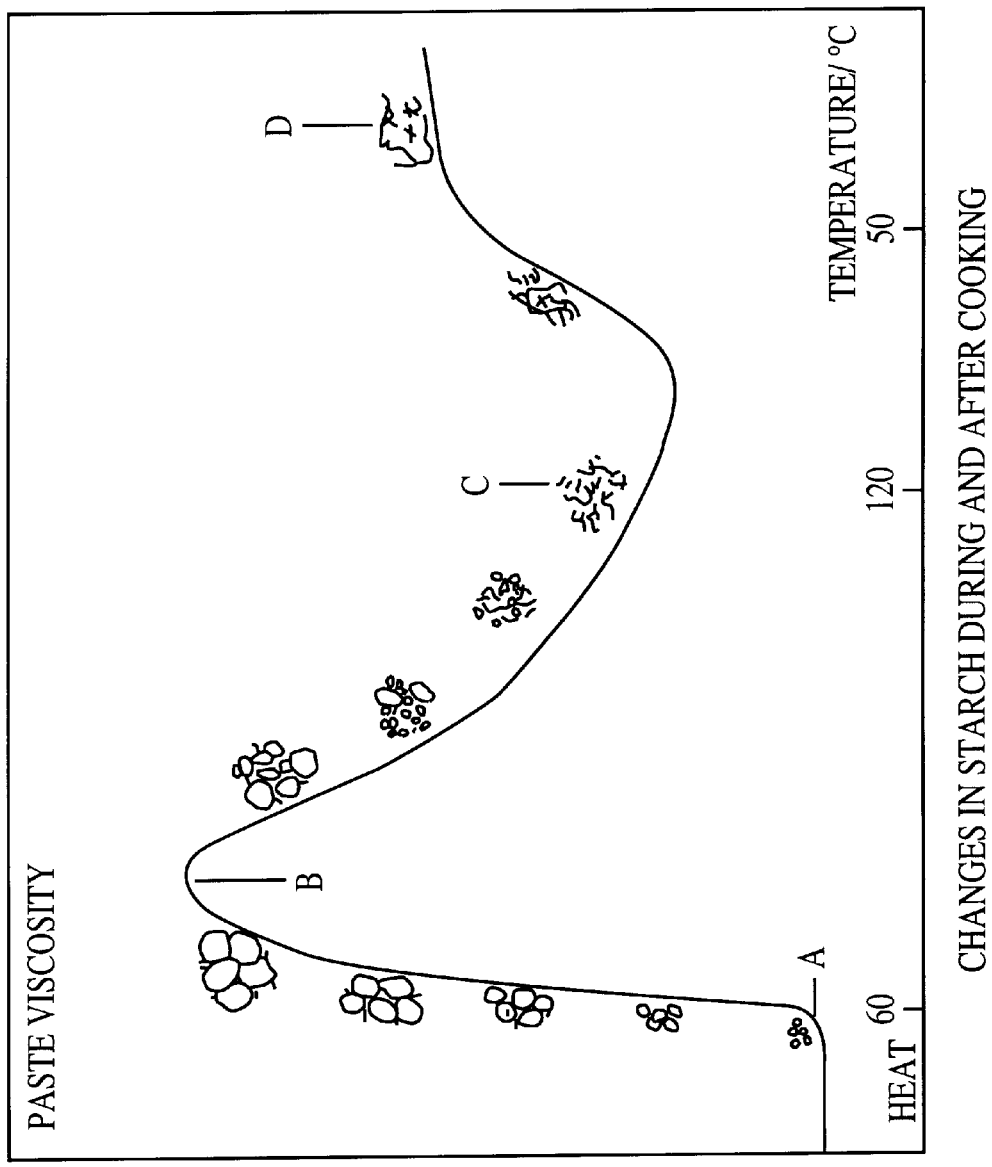
FIG. 2 shows the typical viscosity profile of conventional starch during and after cooking, together with representations of the physical state of starch granules at various stages.

Construction of Plant Transformation Vectors containing Antisense Starch Branching Enzyme Genes (a) Construction of Enhanced 35S Antisense Potato Starch Branching Enzyme Plant Transformation Vector Initally a 1.4 kb EcoRI partial length cDNA for potato starch branching enzyme was purchased from the Agricultural Genetics Company (Cambridge, UK). This cDNA was isolated from a lambda phage library (methylase protected fragments) made from RNA extracted from potato tubers (cv Desiree) using standard techniques (Sambrook. Fritsch & Maniatis, (1989) Molecular Cloning: A Laboratory Manual, Cold Spring Harbor Lab, NY, 2nd Ed). Subsequently a partial cDNA clone of about 2.3 kb was isolated containing an additional 0.9 kb of sequence 3' to the original cDNA and including the polyadenylated tail.

Even later a full length clone was obtained and sequenced (shown in FIG. 8. Seq ID No. 1). although only partial cDNA clones had been isolated by the time antisense experiments (described below) were conducted. The full length sequence shown in FIG. 8 is in reasonably close agreement with the full length sequence of potato SBE disclosed by Poulsen & Kreiberg (1993, Plant Physiol. 102, 1053–1054), although some differences are readily apparent. Other SBE sequences have also been described (Jens Rossmann PhD Thesis. Lebensmitteltechnologie und Biotechnologie der Technischen Universitat Berlin 1992), and again, there are sequence differences with the sequence shown in FIG. 8. Nevertheless, in principle, it should prove possible to use sequences derived from, or based on, those disclosed in the prior art to obtain the present invention.

The 5' end of the two partial cDNAs obtained by the inventors had the same EcoRI site (at nucleotides 615–620 in FIG. 8). The 3' end of the 2.3 kb clone is at nucleotide 3080 of FIG. 8 (which includes an EcoRI linker). The 2.3 kb EcoRI fragment was subcloned in an antisense orientation between the duplicated cauliflower mosaic (CaMV) virus 35S promoter (Cabb-JI strain, equivalent to nucleotide 7040 to 7376 duplicated upstream of 7040 to 7433) and the CaMV polyadenylation signal in 7435–126 (Franck A, Guilley H, Jonard G. Richards R and Hirth L (1980) Cell 21, 285–294) in the vector pJIT 60 (Guerineau et al., (1992) Plant Mol. Biol: 18, 815–818). The promoter-antisense potato starch branching enzyme-polyA fragment was then cloned into the plant transformation vector BIN19 (Bevan M (1984) Nucl. Acids Res. 12, 8711–8721).

(b) Construction of Patatin Promoter Antisense Potato Starch Branching Enzyme Plant Transformation Vector The 2.3 kb EcoRI fragment (corresponding to about ⅔ of the full length cDNA) of the potato starch branching enzyme was subcloned into the EcoRI site of the pBSSK II plus vector (Stratagene) to create pSJ5. A XhoI (Klenow repaired) SacI fragment containing the SBE fragment from pSJ5 was subcloned into pBI140.5 cut with SmaI and SacI; this places the SBE in an antisense orientation with respect to the promoter. The resulting plasmid was termed pSJ7. For information. pBI140.5 is a BIN19 derivative containing a 3.5 kb Patatin type I promoter (HindIII to DraI of PAT21, Bevan M, Barker R, Goldsborough A. Jarvis M, Ravanagh T & Iturriaga G (1986) Nucl. Acids Res. 14, 4625–4638) and the polyadenylation signal of the nopaline synthase (Bevan M. Barnes W & Chilton M-D. Nucl. Acids Res. 11, 369–385). *E. coli* strain DH5α was transformed with pSJ7 using standard techniques and the transformant deposited at the National Collections of Industrial and Marine Bacteria, 23 St Machar Drive, Aberdeen AB2 1RY, United Kingdom (date of deposit: Feb. 12, 1994; accession number NCIMB 40701).

(c) Transformation of *Agrobacterium tumefaciens*

The plant transformation vectors containing antisense branching enzyme genes were transferred into *A. tumefaciens* (C58/pGV3850) using a direct DNA uptake protocol [An et al., Binary Vectors, In: Plant Molecular Biology Manual (ed. Galvin and Schilperoort) A3 (1988) 1–19].

Example 2

Transformation of Potato with Antisense Starch Branching Enzyme Constructs (a) Stock Cultures Stock nodal cutting cultures of potato (cv. Desiree) were maintained on Murashige and Skoog basal media (MS) containing 1% sucrose at 22° C. in an illuminated culture room (40 μjoules/m$^2$/hr) with a 16h day. Cuttings were taken every three weeks. with 5 plantlets grown in each Magenta vessel to produce nodes with large leaves [Westcott R. Proc. 5th Intl. Cong. Plant Tissue and Cell Culture (1982), ed. Fujiwara, Tokyo]. Establishment of plants into compost was as described by Westcott (1982).

(b) Tuberisation

Tuberisation was achieved by transfer of single nodes to MS media containing 8% sucrose and 2.5 mg/l benzylaminopurine (BAP) and incubating in darkness at 22° C. After tuberisation had proceeded to pea-sized tubers the explants could be transferred to Magenta vessels containing the same media for storage of up to 6 months.

(c) Agrobacterium Infection

Halved in vitro tubers were incubated with log phase A. tumefaciens cells for 10 min, after which the explant tissue was removed, blotted on filter paper and transferred onto nurse plates. Nurse plates were prepared by plating 2 ml Nicotiana plumbaginofolia suspension cells (Barfield et al., Plant Cell Reports 4, 104–107 (1985)) onto regeneration media (0.8% Bactoagar, MS salts, 1% sucrose, 0.2 mg/l indole acetic acid (IAA), 5 mg/l zeatin). Explants were incubated under illumination for 2 days before transfer to fresh regeneration media containing 500 mg/l cefotaxime. 5 days later explants were transferred to the same media containing 100 mg/l kanamycin. After 4 weeks (2 transfers) explants were transferred onto expansion media (MS salts, 1% sucrose. 1.0 mg/l gibberellic acid (GA3) containing cefotaxime and kanamycin. After a total of 8 weeks, regenerating shoots were removed and transferred to basal media (MS salts, 1% sucrose) containing cefotaxime and kanamycin.

(d) Growth of Plants

Rooted regenerants, 1–2 cm high, were transferred to compost (50% Levingtons/50% grit) and grown under high illumination (400 μjoules/m$^2$/hr) at 20° C. day and 18° C. night with a 16 hr day period. After 10–12 days, plantlets transferred to 3" pots containing Arthur Bowes Universal Compost. After establishment (40 days), four plants from each clone were repotted together in 10" pots with same compost. Dav length was reduced to 11 hr after approximately 100 days growth. Tubers were harvested after foliage senescence (approximately 120 days).

Example 3

Analysis of Transgenic Plants (a) Southern Analysis

DNA was isolated from leaves of regenerated plants (Dellaporta, Plant Mol. Biol. Reporter 1, 19–21 (1983)), digested with EcoRI, electrophoresed in a 1% agarose gel in TBE buffer, transferred to Genescreen in 20×SSC and u.v. cross-linked (Stratalinker, Stratgene). Blots were hybridised to random-prime labelled (Amersham) 2.3 kb EcoRI potato starch branching enzyme fragment in 5×SSPE (0.9M NaCl, 50 mM NaH$_2$PO$_4$, 5 mM EDTA), 5×Denhardts solution, 1% SDS, 100 μg/ml denatured salmon sperm DNA at 65° C. overnight. Final washing stringency was 0.2×SSC, 1% SDS at 65° C. for 15 min. Positive transformants were identified by hybridisin 1.4 and 0.9 kb fragments (endogenous SBE genes produced higher molecular weight hybridising fragments, presumably due to the presence of introns).

(b) Starch Branching Enzyme (SBE) Assay of Transgenic Tubers

Sample tubers from each plant were taken after harvest, washed and stored at −20° C. until assay.

Frozen tubers were crushed in a mortar and pestle in 2 vol. extraction buffer cooled to 4° C. The buffer contained 100 mM 2-amino-2-(hydroxymethyl)-1,3 propanediol (Tris) pH 7.5, 10 mM ethylene-diaminetetra-acetic acid (EDTA), 2.5 mM dithiotlreitol (DTT), 0.1% (w/v) sodium metabisulphite and 10% (w/v) polyvinyl-polypyrrolidone (PVPP). When completely homogenised the crude homogenate was clarified by centrifuging at 10.000 g for 10 minutes. The supernatant was retained for the assay of starch branching enzyme activity.

The standard SBE assav reaction mixture, in a volume of 0.2 ml, was 200 mM 2-(N-morpholino) ethanesulphonic acid (MES) buffer, pH 6.5, 50 mM[$^{14}$C]glucose 1-phosphate (100 nCi), 0.05 mg rabbit phosphorylase A and potato tuber extract. Incubations were performed at 30° C. for 60 minutes. Negative controls contained either: (a) no phosphorylase, or (b) the potato tuber extract boiled for 30 minutes to destroy enzyme activity. The reaction was terminated and glucan polymer precipitated by the addition of 1 ml of 75% (v/v) methanol, 1% (w/v) potassium hydroxide (KOH) and then 0.1 ml of glycogen (10 mg ml 1). Insoluble glucan polymer was pelleted by centrifugation and washed with a further 1 ml of methanol/KOH before being redissolved in water and the incorporated radioactivity measured in a Beckman LS 3800 liquid scintillation counter.

Activity was expressed as units. with one unit defined as 1 micromole of glucose incorporated per minute. All measurements were taken during the phase of the assay when the rate of glucose incorporation was linear.

The results are shown in Table 1. For the transgenic plants it can be seen that, relative to control values, SBE activity has been reduced by varving degrees. Several plants have SBE activities less than 0.8 U/g tuber (below 10% of average control values).

Starch Branching Enzyme Assays of Transgenic Potato Tuber Extracts

All starch branching enzyme activities were measured in duplicate and mean values taken. At low levels of activity absolute quantitation, via the standard phosphorylase assay, is more difficult because inacurracies introduced by background activity are proportionally much greater.

| POTATO TUBER STARCH BRANCHING ENZYME ACTIVITY | | |
|---|---|---|
| | PLANT | ACTIVITY (units g$^{-1}$ tuber) |
| CONTROL | 58 | 21.3 |
| | 40 | 18.2 |
| | 31 | 16.6 |
| | 29 | 13.1 |
| | 49 | 13.0 |
| | 8 | 12.7 |
| Pat AS 2/3 Pot | 47 | 2.8 |
| | 54 | 2.4 |
| | 69 | 0.2 |
| 2 × 35S AS ⅔ Pot | 25 | 16.9 |
| | 5 | 13.0 |
| | 9 | 13.0 |
| | 32 | 12.5 |
| | 16 | 12.2 |
| | 6 | 11.1 |
| | 22 | 7.7 |
| | 23 | 7.6 |
| | 20 | 6.6 |
| | 26 | 5.5 |
| | 34 | 5.2 |
| | 14 | 4.6 |
| | 24 | 4.6 |
| | 61 | 4.5 |
| | 4 | 4.3 |
| | 21 | 3.9 |
| | 19 | 2.4 |

-continued

POTATO TUBER STARCH BRANCHING ENZYME ACTIVITY

| PLANT | ACTIVITY (units g$^{-1}$ tuber) |
|---|---|
| 17 | 2.3 |
| 28 | 2.3 |
| 18 | 1.9 |
| 3 | 1.8 |
| 13 | 1.4 |
| 10 | 1.1 |
| 2 | 1.0 |
| 1 | 0.7 |
| 53 | 0.6 |
| 27 | 0.6 |
| 12 | 0.5 |
| 15 | 0.5 |
| 33 | 0.5 |
| 52 | 0.5 |
| 11 | 0.4 |
| 60 | 0.4 |
| 7 | 0.4 |
| 72 | 0.3 |
| 68 | 0.3 |
| 35 | 0.2 |

Example 4

Analysis of Transgenic Starch Properties (a) Starch Extraction

Potato tubers were homogenised in water for 2 min in a Waring blender operating at high speed. The homogenate was washed and filtered (initially 2 mm, then 1 mm filters) using approximately 4L of water per 100 g of tubers (6 extractions). Washed starch granules were finally extracted with acetone and air dried.

(b) Differential Scanning Calorimetry

Figure 3:
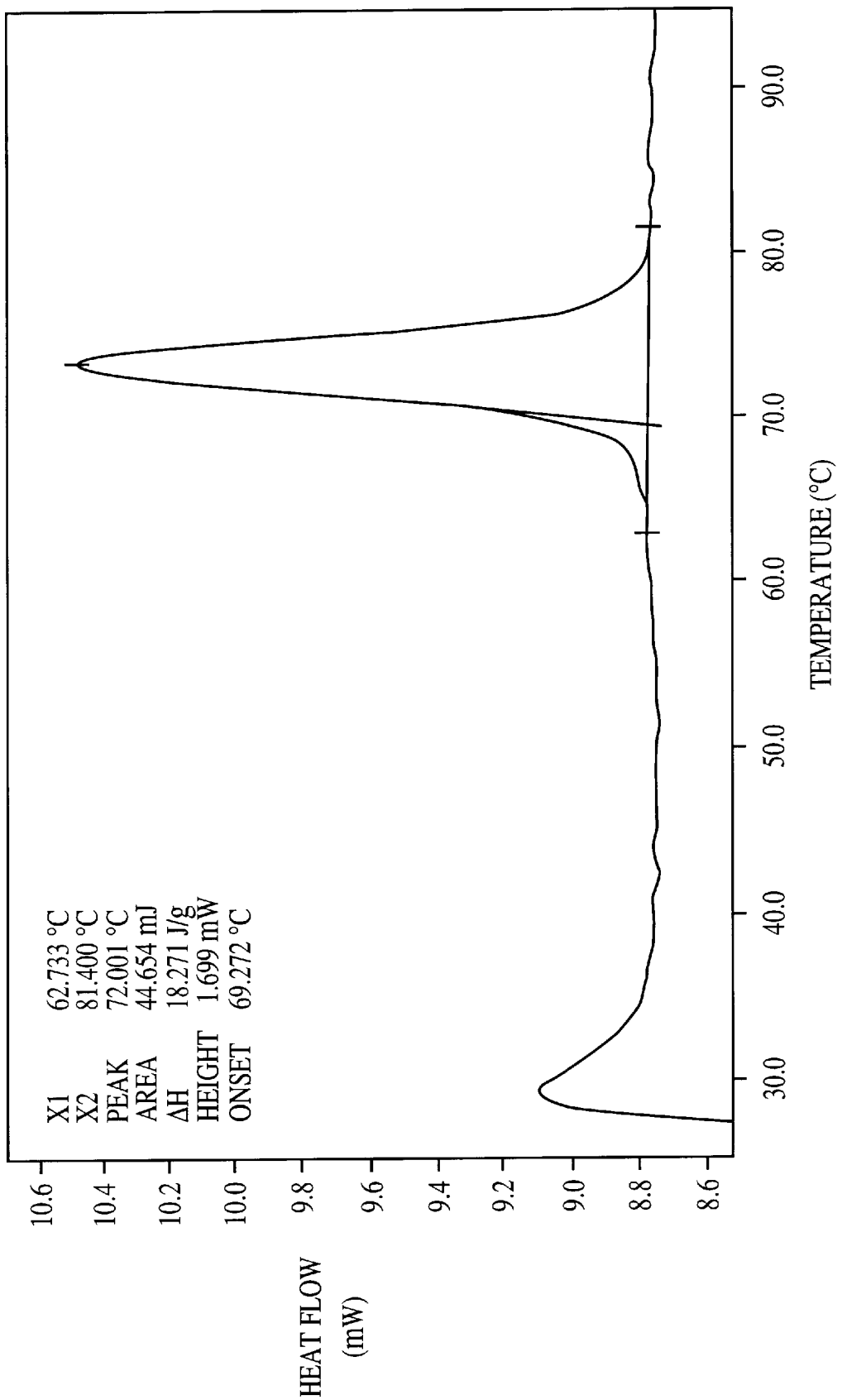
FIG. 3 shows how the degree of gelatinisation of a sample of altered starch in accordance with the invention varies with temperature as measured by differential scanning calorimetry (DSC)

The temperature range for the loss of granule order upon heating starches in excess water was determined by differential scanning calorimetry. Starch powders isolated from a range of transgenic potato plants were analyses using the Perkin Elmer DSC 7 instrument. 1–4 mg of starch was accurately weighed into an aluminium sample pan, and water added so that the starch concentration was less than 25% w/v, to give a total sample weight of 10–15 mg. An empty reference sample pan was used. A heating rate of 10° C./minute was used to heat the test and reference samples from 25° C. to 95° C. Data analysis was performed using the instrument software. Examples of results are shown in FIGS. 1 and 3. A number of temperature parameters can be obtained from such plots, the most accurate being the peak temperature. A difference in peak temperature of 2–3° C. is readily determined as shown by comparison of FIG. 1 (peak temperature 69.3° C.) and FIG. 3 (peak temperature 72.0° C.).

Figure 4:
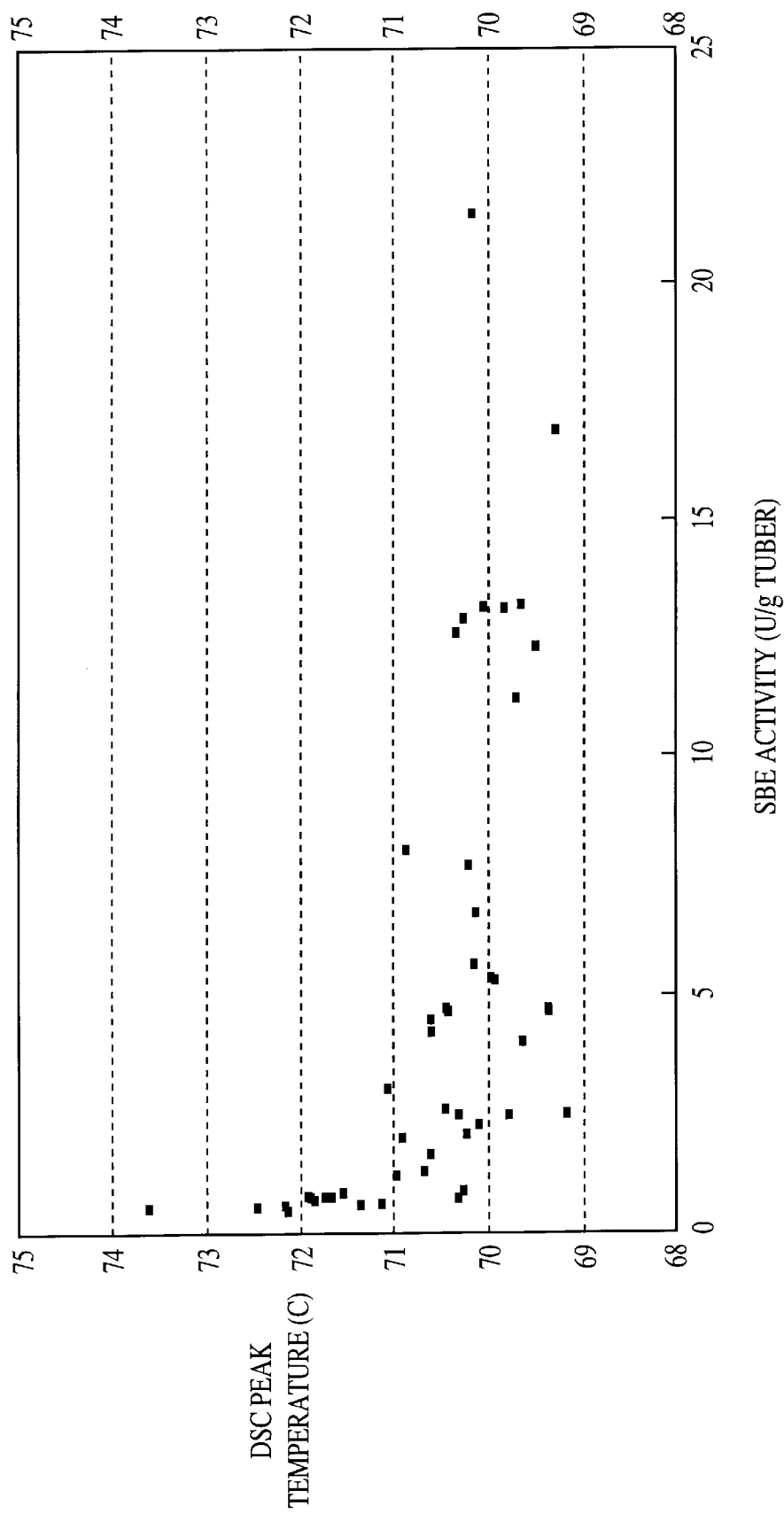
FIG. 4 is a graph of peak temperature of gelatinisation (° C.) (as measured by DSC) against SBE activity (Units), showing how the two parameters are correlated.

Starches isolated from potato plants exhibiting a range of starch branching enzyme activities (determined as described in Example 3b) were characterised by differential scanning calorimetry. Peak temperatures are compared with starch branching enzyme activity in FIG. 4. from which it appears that levels of enzyme activity less than 0.8 U/g of tuber are required for consistent increases in peak temperature.

(c) Viscosity Development

Figure 5:
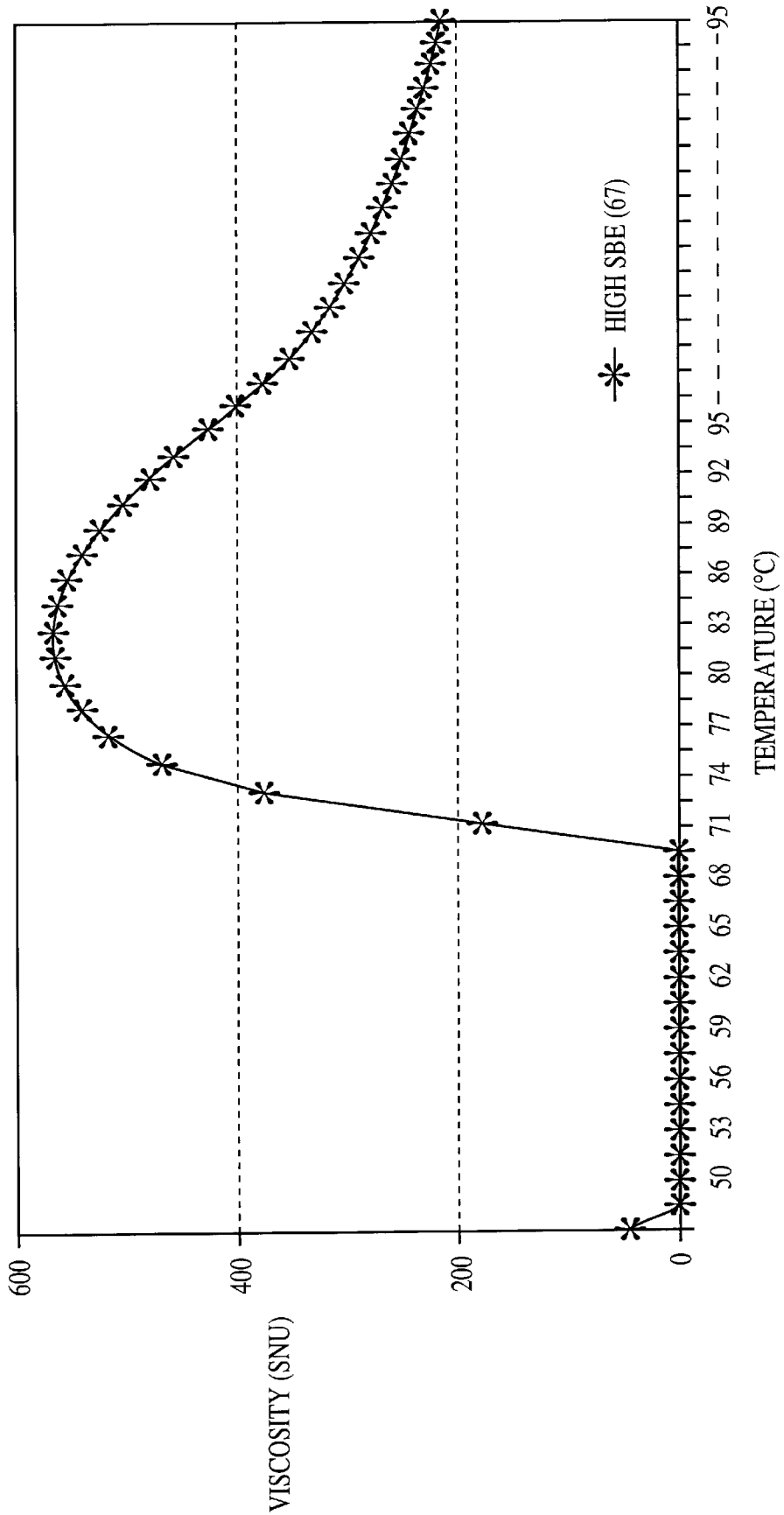
FIG. 5 is a graph of viscosity (SNU) against temperature (° C.) for unaltered starch.

Starches isolated from a range of transgenic potato plants were analysed for viscosity development ('pasting') following the loss of granule order. The instrument used was the Rapid Visco Analyser 3C (Newport Scientific, Sydney, Australia). Starch (2.50 g) was weighed into an instrument sample holder, and water (22.50 g) added so that the final concentration was 10% w/w starch. Suspensions were equilibrated for 2 minutes at 50° C. and heated under standard stirring conditions at 1.5° C. minute from 50° C. to 95° C., then held at 95° C. for 15 minutes. The viscosity developed was measured in instrument stirring number units (SNU). A typical trace obtained is shown in FIG. 5. The broad maximum observed as a function of temperature makes the accurate determination of a peak temperature difficult, but the fact that viscosity starts from a very low level and rapidly rises allows an accurate determination of a viscosity onset temperature, defined as the temperature at which viscosity is at least 50% higher than at all lower temperatures above 50° C.

Figure 6:
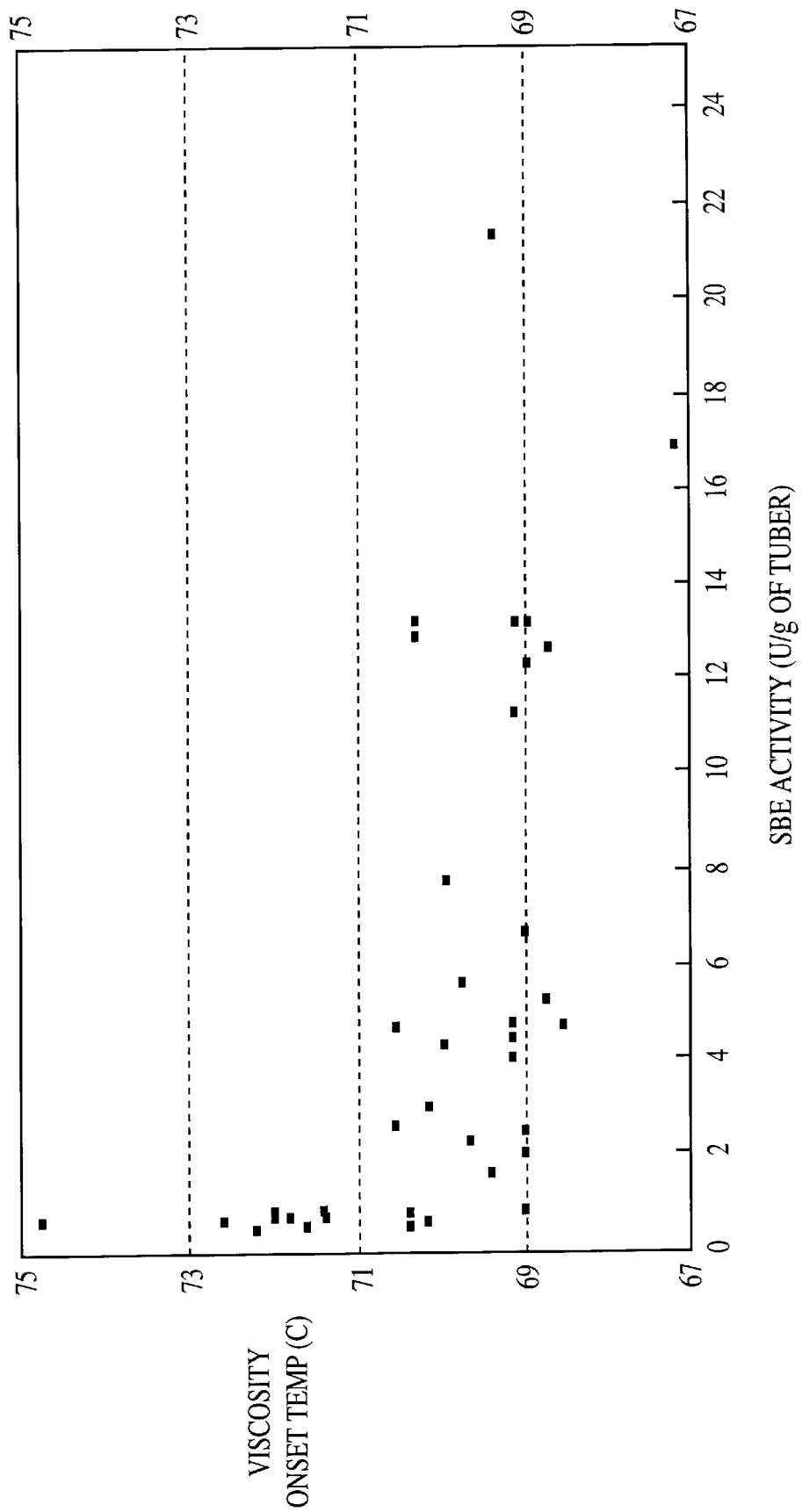
FIG. 6 is a graph of viscosity onset temperature (° C.) against SBE activity (Units), showing how the two parameters are related.
Figure 7:
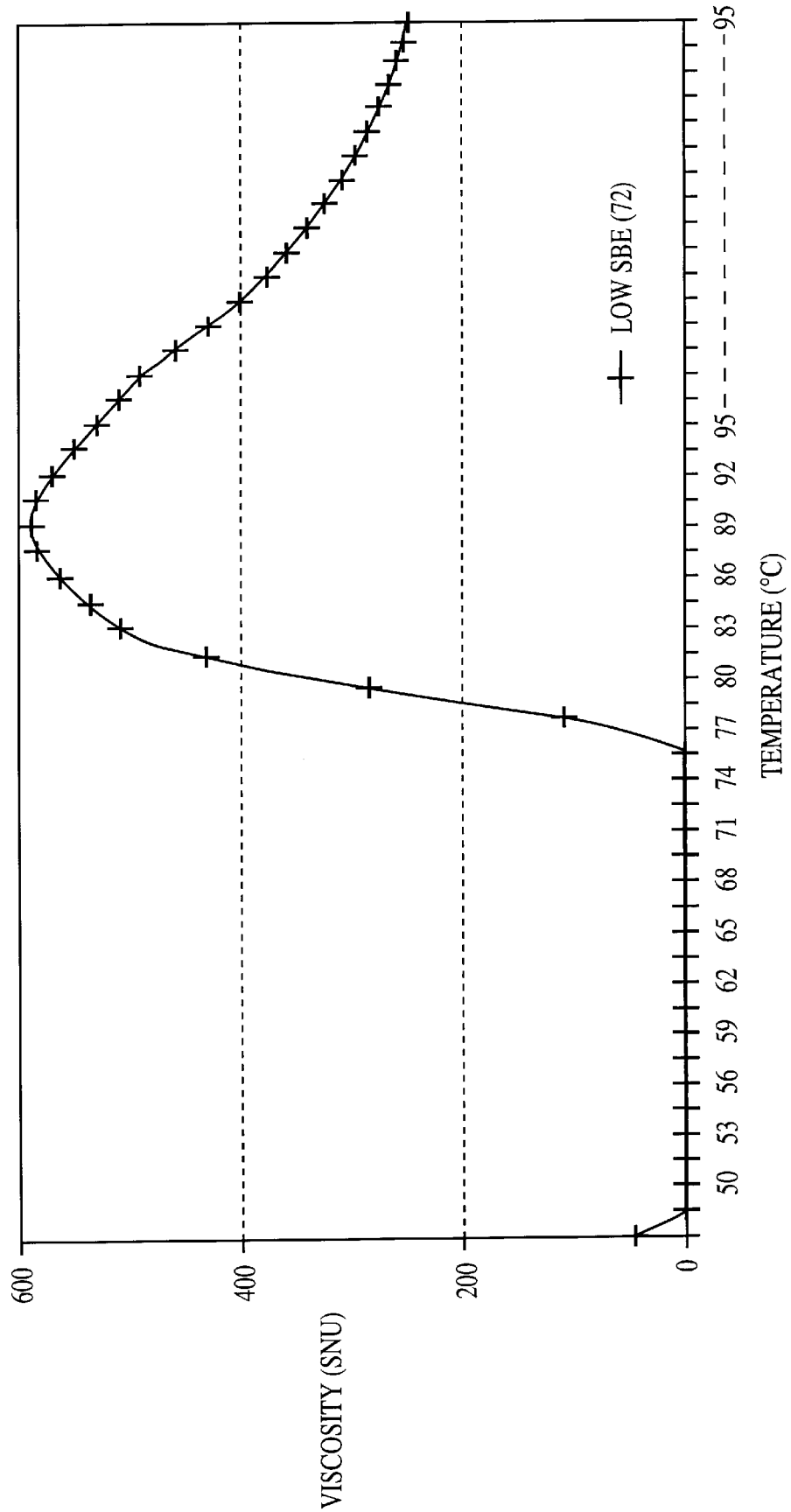
FIG. 7 is a graph of viscosity (SNU) against temperature (° C.) for altered starch in accordance with the invention.

The viscosity onset temperatures for starches isolated from potato plants exhibiting a range ot starch branching enzyme activities were determined, with the results shown in FIG. 6. These data show that a consistent increase in viscosity onset temperature is found for starches from plants containing less than 0.8 U/g of tuber of starch branching enzyme. For those starches which show a higher viscosity onset temperature, other parameters of pasting (e.g. peak temperature) are also higher. This is illustrated by comparison of FIGS. 5 (onset temperature: 70° C. peak temperature: 82° C.) and 7 (onset temperature 75° C., peak temperature: 87° C.).

Example 5

Construction of GBSS antisense full lenoth potato starch branching enzyme vector The inventors have recently made a further construct comprising a full length potato SBE cDNA in the anti-sense orientation under the control of the GBSS promoter. Details of the construction are given below. No experimental data regarding this construct are yet available.

A full length cDNA clone for potato starch branching enzyme corresponding to nucleotides 91–3114 plus an additional 10 bases at the 3' end (Poulsen, P. & Kreiberg, J. D. Plant Physiol. (1993) 102: 1053–1054) was isolated from a potato tuber cDNA library (see above). The cDNA was excised from the plasmid vector by cutting with SacI and XhoI and inserted in an antisense orientation between the granule bound starch synthase promoter (GBSS) and the nos polyadenylation signal in the BIN 19 based plant transformation vector pPGB121 which had been cut with SacI and SalI. The GBSS promoter is a 0.8 kb HindIII-NsiI fragment of the granule bound starch synthase genomic clone LGBSSwt-6; this promoter fragment directs GUS expression in an organ specific manner (up to 3350 fold higher in tubers than in leaves and up to 25 fold higher than the CaMV promoter) (Visser, R G F. Stollte, A. and Jacobsen, E. Plant Mol. Biol. (1991) 17:691–699).

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 3128 base pairs
      (B) TYPE: nucleic acid
      (C) STRANDEDNESS: single
      (D) TOPOLOGY: linear (ii) MOLECULE TYPE:
      (A) DESCRIPTION: cDNA encoding starch branching enzyme (iii) HYPOTHETICAL: No (iv) ANTI-SENSE: No (v) FRAGMENT TYPE:

(vi) ORIGINAL SOURCE: clone 1.2.1 and E2
      (A) ORGANISM: Solanum tuberosum
      (B) STRAIN: cv desiree
      (C) INDIVIDUAL ISOLATE:
      (D) DEVELOPMENTAL STAGE: mature tuber
      (E) HAPLOTYPE:
      (F) TISSUE TYPE:
      (G) CELL TYPE:
      (H) CELL LINE:
      (I) ORGANELLE:

(vii) IMMEDIATE SOURCE:
      (A) LIBRARY: lambda Zap tuber cDNA
      (B) CLONE: 1.2.1 and E2

(viii) POSITION IN GENOME:
      (A) CHROMOSOME/SEGMENT:
      (B) MAP POSITION:
      (C) UNITS:

(ix) FEATURE: open reading frame
      (A) NAME/KEY: starch branching enzyme
      (B) LOCATION: 44-2788
      (C) IDENTIFICATION METHOD: lone ORF with homology to other starch
         branching enzymes
      (D) OTHER INFORMATION: complements KV832 E. coli glycogen
         branching enzyme mutant (xi) SEQUENCE DESCRIPTION:SEQ ID NO:1:

```
GAATTCGGCA CGAGAGCTGA AGCAAAGTAC CATAATTTAA TCAATGGAAA TTAATTTCAA      60

TGTTTTGTCA AAACCCATTC GAGGATCTTT TCCATCTTCC TCACCTAAAG TTTCTTCAGG     120

GGCTTCTAGA AATAAGATAT GTTTTCCTTC TCAACATAGT ACTGGACTGA AGTTTGGATC     180

TCAGGAACGG TCTTGGGATA TTTCTTCCAC CCCAAAATCA AGAGTTAGAA AAGATGAAAG     240

GATGAAGCAC AGTTCAGCTA TTTCCGCTGT TTTGACCGAT GACAATTCGA CAATGGCACC     300

CCTAGAGGAA GATGTCAAGA CTGAAAATAT TGACCTCCTA AATTTGGATC CAACTTTGGA     360

ACCTTATCTA GATCACTTCA GACACAGAAT GAAGAGATAT GTGGATCAGA AAATGCTCAT     420

TGAAAAATAT GAGGGACCCC TTGAGGAATT TGCTCAAGGT TATTTAAAAT TTGGATTCAA     480

CAGGGAAGAT GGTTGCATAG TCTATCGTGA ATGGGCTCCT GCTGCTCAGG AAGCAGAAGT     540

TATTGGCGAT TTCAATGGAT GGAACGGTTC TAACCACATG ATGGAGAAGG ACCAGTTTGG     600

TGTTTGGAGT ATTAGAATTC CTGATGTTGA CAGTAAGCCA GTCATTCCAC ACAACTCCAG     660

AGTTAAGTTT CGTTTCAAAC ATGGTAATGG AGTGTGGGTA GATCGTATCC CTGCTTGGAT     720
```

-continued

| | | | | | |
|---|---|---|---|---|---|
| AAAGTATGCC | ACTGCAGACG | CCACAAAGTT | TGCAGCACCA | TATGATGGTG | TCTACTGGGA | 780 |
| CCCACCACCT | TCAGAAAGGT | ACCACTTCAA | ATACCCTCGC | CCTCCCAAAC | CCCGAGCCCC | 840 |
| ACGAATCTAC | GAAGCACATG | TCGGCATGAG | CAGCTCTGAG | CCACGTGTAA | ATTCGTATCG | 900 |
| TGAGTTTGCA | GATGATGTTT | TACCTCGGAT | TAAGGCAAAT | AACTATAATA | CTGTCCAGTT | 960 |
| GATGGCCATA | ATGGAACATT | CTTACTATGG | ATCATTTGGA | TATCATGTTA | CAAACTTTTT | 1020 |
| TGCTGTGAGC | AATAGATATG | GAAACCCGGA | GGACCTAAAG | TATCTGATAG | ATAAAGCACA | 1080 |
| TAGCTTGGGT | TTACAGGTTC | TGGTGGATGT | AGTTCACAGT | CATGCAAGCA | ATAATGTCAC | 1140 |
| TGATGGCCTC | AATGGCTTTG | ATATTGGCCA | AGGTTCTCAA | GAATCCTACT | TTCATGCTGG | 1200 |
| AGAGCGAGGG | TACCATAAGT | TGTGGGATAG | CAGGCTGTTC | AACTATGCCA | ATTGGGAGGT | 1260 |
| TCTTCGTTTC | CTTCTTTCCA | ACTTGAGGTG | GTGGCTAGAA | GAGTATAACT | TTGACGGATT | 1320 |
| TCGATTTGAT | GGAATAACTT | CTATGCTGTA | TGTTCATCAT | GGAATCAATA | TGGGATTTAC | 1380 |
| AGGAAACTAT | AATGAGTATT | TCAGCGAGGC | TACAGATGTT | GATGCTGTGG | TCTATTTAAT | 1440 |
| GTTGGCCAAT | AATCTGATTC | ACAAGATTTT | CCCAGACGCA | ACTGTTATTG | CCGAAGATGT | 1500 |
| TTCTGGTATG | CCGGGCCTTA | GCCGGCCTGT | TTCTGAGGGA | GGAATTGGTT | TTGATTACCG | 1560 |
| CCTGGCAATG | GCAATCCCAG | ATAAGTGGAT | AGATTATTTA | AAGAATAAGA | ATGATGAAGA | 1620 |
| TTGGTCCATG | AAGGAAGTAA | CATCGAGTTT | GACAAATAGG | AGATATACAG | AGAAGTGTAT | 1680 |
| AGCATATGCG | GAGAGCCATG | ATCAGTCTAT | TGTCGGTGAC | AAGACCATTG | CATTTCTCCT | 1740 |
| AATGGACAAA | GAGATGTATT | CTGGCATGTC | TTGCTTGACA | GATGCTTCTC | CTGTTGTTGA | 1800 |
| TCGAGGAATT | GCGCTTCACA | AGATGATCCA | TTTTTTCACA | ATGGCCTTGG | GAGGAGAGGG | 1860 |
| GTACCTCAAT | TTCATGGGTA | ACGAGTTTGG | CCATCCTGAG | TGGATTGACT | TCCCTAGAGA | 1920 |
| GGGCAATAAT | TGGAGTTATG | ACAAATGTAG | ACGCCAGTGG | AACCTCGCAG | ATAGCGAACA | 1980 |
| CTTGAGATAC | AAGTTTATGA | ATGCATTTGA | TAGAGCTATG | AATTCGCTCG | ATGAAAAGTT | 2040 |
| CTCATTCCTC | GCATCAGGAA | ACAGATAGT | AAGCAGCATG | GATGATGATA | ATAAGGTTGT | 2100 |
| TGTGTTTGAA | CGTGGTGACC | TGGTATTTGT | ATTCAACTTC | CACCCAAATA | ACACATACGA | 2160 |
| AGGGTATAAA | GTTGGATGTG | ACTTGCCAGG | GAAGTACAGA | GTTGCACTGG | GCAGTGATGC | 2220 |
| TTGGGAATTT | GGTGGCCATG | GAAGAGCTGG | TCATGATGTT | GACCATTTCA | CATCACCAGA | 2280 |
| AGGAATACCT | GGAGTTCCAG | AAACAAATTT | CAATGGTCGT | CCAAATTCCT | TCAAAGTGCT | 2340 |
| GTCTCCTGCG | CGAACATGTG | TGGCTTATTA | CAGAGTTGAT | GAACGCATGT | CAGAAACTGA | 2400 |
| AGATTACCAG | ACAGACATTT | GTAGTGAGCT | ACTACCAACA | GCCAATATCG | AGGAAAGTGA | 2460 |
| CGAGAAACTT | AAAGATTCAT | CATCTACAAA | TATCAGTACA | TCATCTACAA | AAAATGCTTA | 2520 |
| TTACAGAGTT | GATGAACGCA | TGTCAGAAGC | TGAAGATTAC | CAGACAGACA | TTTGTAGTGA | 2580 |
| GCTACTACCA | ACAGCCAATA | TCGAGGAGAG | TGACGAGAAA | CTTGATGATT | CATTATCTAC | 2640 |
| AAATATCAGT | AACATTGGTC | AGACTGTTGT | AGTTTCTGTT | GAGGAGAGAG | ACAAGGAACT | 2700 |
| TAAAGATTCA | CCATCTGTAA | GCATCATTAG | TGATGCTGTT | CCAGCTGAAT | GGGCTGATTC | 2760 |
| GGATGCAAAC | GTCTGGGGTG | AGGACTAGTC | AGATGATTGA | TCGATCCTTC | TACGTTGGTG | 2820 |
| ATCTTGGTCC | GTGCATGATG | TCTTCAGGGT | GGTAGCATTG | ACTGATTGCA | TCATAGTTTT | 2880 |
| TTTTTTTTTT | TAAGTATTTC | CTCTATGCAT | ATTATTAGCA | TCCAATAAAT | TTACTGGTTG | 2940 |
| TTGTACATAG | AAAAAGTGCA | TTTGCATGTA | TGTGTTTCTC | TGAAATTTTC | CCCAGTTTTT | 3000 |

-continued

| | |
|---|---|
| GGTGCTTTGC CTTTGGAGCC AAGTCTCTAT ATGTAATAAG AAAACTAAGA ACAATCACAT | 3060 |
| ATATAAAATG TTAGTAGATT ACCATAAAAA AAAAATTAAA AAAAAAAAAA AAAAACTCGA | 3120 |
| GGGGGGGC | 3128 |

The invention claimed is:

1. A method of producing altered starch from transformed potato plants or their progeny, the method comprising extracting starch from a potato plant, at least the tubers of which comprise at least an effective portion of a starch branching enzyme (SBE) cDNA sequence operably linked in the antisense orientation to a suitable promoter, such that the level of SBE activity is limited to less than 0.8 units per gram tuber.

2. The method according to claim 1, wherein the tubers contain at least ⅔ of an SBE cDNA sequence operably linked in the antisense orientation to a suitable promoter.

3. The method according to claim 1, wherein the starch is extracted from plants, the tubers thereof having less than 10% of the SBE activity in equivalent non-transformed plants.

4. The method according to claim 1, wherein the peak temperature of gelantinisation of the starch so produced is elevated by at least 2° C. compared to unaltered starch produced from equivalent non-transformed plants.

5. The method according to claim 1, wherein the viscosity onset temperature of the starch so produced is elevated by at least 3° C. compared to unaltered starch produced from equivalent non-transformed plants.

6. The method according to claim 1, wherein the peak temperature of gelatinisation (as determined by differential scanning calorimetry) of the starch so produced is at least 71° C.

7. The method according to claim 1, wherein the viscosity onset temperature of the starch so produced is at least 71° C.

8. The method according to claim 1, comprising wet milling of potato tubers.

9. An altered starch produced by the method of claim 1.

10. The method according to claim 1, wherein the starch is extracted from plants, the tubers thereof having less than 5% of the SBE activity in equivalent non-transformed plants.

11. The method according to claim 1, wherein the peak temperature of gelatinization of the starch so produced is elevated by at least 5° C. compared to unaltered starch produced from equivalent non-transformed plants.

12. The method according to claim 1, wherein the viscosity onset temperature of the starch so produced is elevated by at least 5° C. compared to unaltered starch produced from equivalent non-transformed plants.

13. An altered starch, wherein the starch is extracted from transformed potato plants or their progeny, the plants having less than 0.8 units SBE activity per gram tuber, and, as extracted, the starch has the following physical properties:
a) elevated peak temperature of gelatinisation as determined by differential scanning calorimetry (DSC) relative to unaltered starch extracted from equivalent non-transformed plants; and
b) elevated viscosity onset temperature, relative to unaltered starch extracted from equivalent non-transformed plants.

14. The altered starch according to claim 13, wherein said starch is extracted from plants, the tubers thereof having less than 10% SBE activity compared to equivalent non-transformed plants.

15. The altered starch according to claim 13, wherein the peak temperature of gelatinisation is elevated by at least 2° C. compared to unaltered starch extracted from equivalent non-transformed plants.

16. The altered starch according to claim 13, wherein the viscosity onset temperature is elevated by at least 3° C. compared to unaltered starch extracted from equivalent non-transformed plants.

17. The altered starch according to claim 13, wherein said starch is extracted from plants, the tubers thereof having less than 5% SBE activity compared to equivalent non-transformed plants.

18. The altered starch according to claim 13, wherein the peak temperature of gelatinization is elevated by at least 5° C. compared to unaltered starch extracted from equivalent non-transformed plants.

19. The altered starch according to claim 13, wherein the viscosity onset temperature is elevated by at least 5° C. compared to unaltered starch extracted from equivalent non-transformed plants.

* * * * *